United States Patent [19]

Meilland

[11] Plant 5,038

[45] Apr. 12, 1983

[54] MINIATURE ROSE PLANT — MEIDDANEGO VARIETY

[75] Inventor: Marie L. Meilland, Antibes, France

[73] Assignee: The Conard-Pyle Company, West Grove, Pa.

[21] Appl. No.: 319,105

[22] Filed: Nov. 6, 1981

[51] Int. Cl.[3] ..... A01H 5/00

[52] U.S. Cl. ..... Plt./10

[58] Field of Search ..... Plt./10

*Primary Examiner*—Robert E. Bagwill

*Attorney, Agent, or Firm*—Burns, Doane, Swecker & Mathis

[57] ABSTRACT

A new and distinct variety of Miniature rose plant is provided which is a sport of Meirov variety. The new variety is identical to Meirov variety with the exception of the flower color which is of a distinctive bright blood red coloration. Such flowers are highly attractive and long lasting.

19 Drawing Figures

SUMMARY OF THE INVENTION

The present new and distinct variety of Miniature rose plant resulted as a sport of the Meirov variety which is protected in a number of European countries by Breeder's Rights legislation, but is unpatented in the United States. Such Meirov parent variety has been marketed in Europe under the Meillandina trademark of the Universal Rose Selection Meilland et Cie. The parent Meirov variety possesses a different flower coloration than the present variety, but in all other respects is identical to the present variety. More specifically, the parent Meirov variety forms flowers of currant red with a canary yellow halo at the center. The present variety is distinguished from its parent by the formation of highly attractive flowers which are bright blood red in coloration.

The variety claimed herein is characterized as follows:

From the physical standpoint the plant has medium green adult wood and a bushy growth habit, and forms double flowers which are blood red in color wherein the petals are yellowish at the base and possess a great degree of substance; and from the biological standpoint the plant has vigorous vegetation, is well adapted to hot culture, is resistant to disease, and has the ability to hold its flowers for a long period of time.

At the time of the filing of this application the present variety has not yet been protected in any country, nor has the present variety been placed on sale or used in a non-experimental manner in the United States.

Successive generations of asexual propagation by both cuttings and budding have shown that the new variety is stable and that the characteristics of this sport are uniformly passed from generation to generation.

The rose plant of the new variety has been named the Meidanego variety.

BRIEF DESCRIPTION OF THE PHOTOGRAPH

The accompanying photograph shows as nearly true as it is reasonably possible to make the same in a color illustration of this character, typical specimens of plant parts of the new variety illustrated in:

FIG. 1 — a specimen of young stem with foliage;

FIG. 2 — a specimen of inflorescence showing 4 buds before the opening of the sepals;

FIG. 3 — two specimens of buds at the opening of the sepals;

FIG. 4 — two specimens of buds at the opening of the petals;

FIG. 5 — a specimen of a flower in the course of opening;

FIG. 6 — a specimen of a flower when almost fully open — plan view — obverse;

FIG. 7 — a specimen of a flower when almost fully open — plan view — reverse;

FIG. 8 — a specimen of a flower at the end of the blooming cycle — plan view — obverse;

FIG. 9 — a specimen of a flower at the end of the blooming cycle — plan view — reverse;

FIG. 10 — a specimen of a petal as seen from above;

FIG. 11 — a specimen of a petal as seen from below;

FIG. 12 — a specimen of a floral receptacle as seen from above;

FIG. 13 — a specimen of a floral receptacle with the petals removed showing the arrangement of stamens as well as a false petal;

FIG. 14 — a specimen of a floral receptacle showing the arrangement of pistils (petals, sepals, and stamens removed);

FIG. 15 — a specimen of a mature main branch;

FIG. 16 — a specimen of a floral branch;

FIG. 17 — a specimen of a leaf with three leaflets — upper surface;

FIG. 18 — a specimen of a leaf with five leaflets — under surface; and

FIG. 19 — a specimen of a leaf with seven leaflets — upper surface.

DETAILED DESCRIPTION

Figures 1, 2, 3, 4, 5, 6, 7, 8, 9, 10, 11, 12, 13, 14, 15, 16, 17, 18, 19:
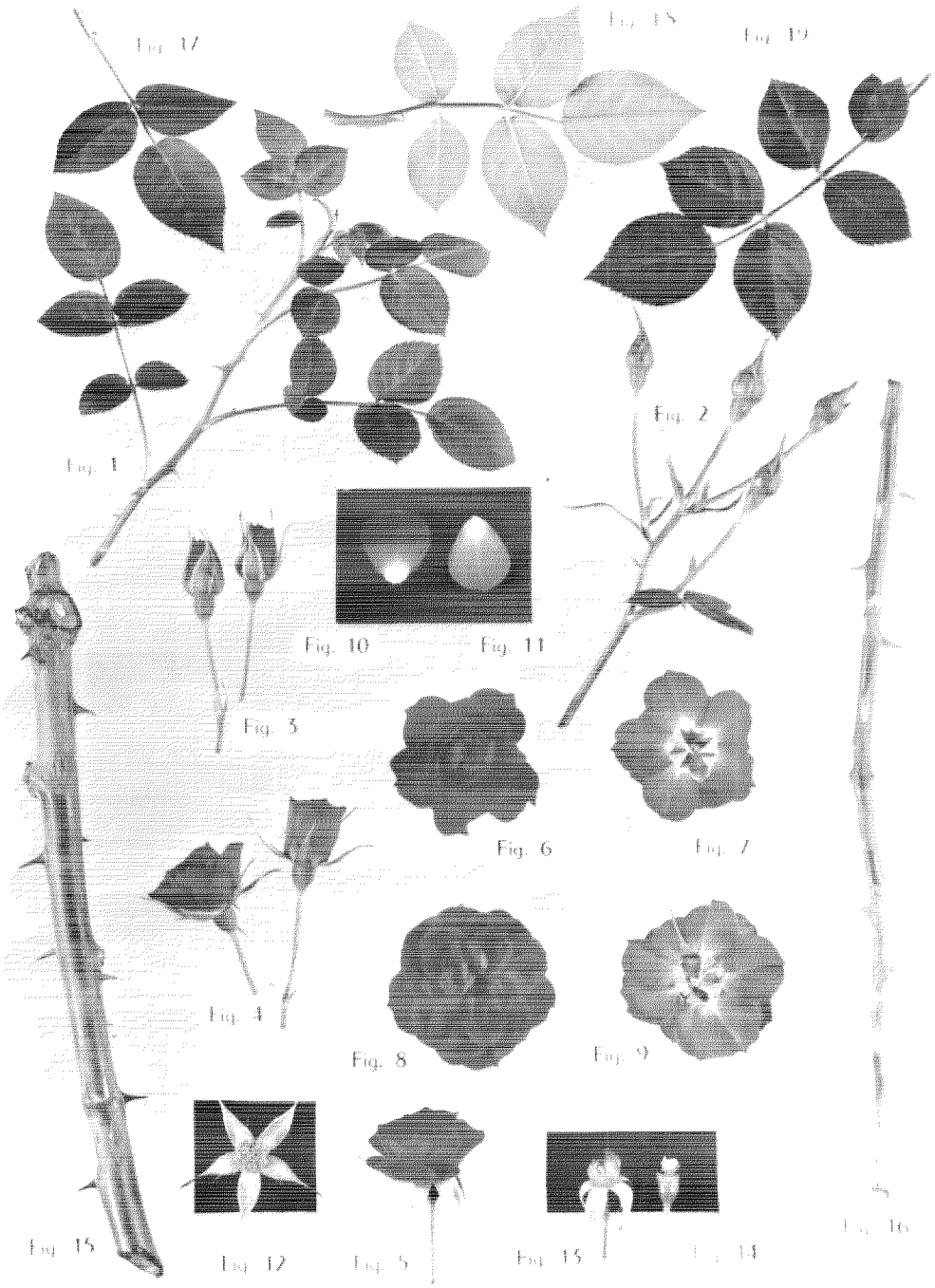

The chart utilized in the identification of the colors is that of The Royal Horticultural Society (R.H.S. Colour Chart) except when general color references are made. The terminology preceding the numbered references to this chart has been added to designate in common terms the corresponding colors.

Class: Miniature.

Plant:

*Height.*—Approximately 40 to 50 cm.

*Habit.*—Bushy.

Branches:

*Color.*—Young stems, Yellow-Green Group 144B. Mature stems, Yellow-Green Group 146B.

Foliage:

*Leaves.*—Compound of usually 5 leaflets, but also 3 or 7 leaflets in number. On some leaves there is occasionally one leaflet missing. Upper surface is grooved and slightly glandular. Under surface commonly possesses several small hooked thorns.

*Leaflets.*—Elliptic with a rounded base which is somewhat symmetrical, apex is large and symmetrical. Color: young foliage: Upper surface: Yellow-Green Group 146A. Under surface: Yellow-Green Group 147C. Color: mature foliage: upper surface: Yellow-Green Group 147A. Under surface: Yellow-Green Group 147B.

Flowers:

*Number of flowers.*—Approximately 3 to 19 per stem.

*Length of bloom.*—Very long.

*Fragrance.*—None.

*Peduncle.*—Straight, rigid, covered with a large number of small glands, length of approximately 2.6 to 3 cm.

*Sepals.*—Tomentose and greenish on the upperside, and light green sometimes with a touch of rouge and more or less glandular on the underside.

*Bud.*—Shape: globular at the opening of the sepals, then gradually changing to a cylindrical configuration. Size: average length of approximately 1.5 cm., medium size. Color: at the opening: upper surface: brilliant, Red Group 45A. Under surface: dull, Red Group 45B.

*Bloom.*—Size when fully open: averages approximately 4.6 cm. in diameter. Petalage: double, approximately 30 to 35 petals, have a great degree of substance, are rounded with apex forming a small point, base of petal on both sides is yellowish in color. Form: just as the sepals open the bud is somewhat flat with a sunken center and becomes fairly flat in form as the flower continues to open. Color: at the opening — inside surface: blood red, Red Group, 45B. Outside surface: cherry red, Red Group 45C, and somewhat dull. Color: completely open — inside surface: blood red, Red Group 45B. Outside surface: Cherry red, Red Group 45C. Color: end of bloom — inside surface: blood red, somewhat lighter than Red Group 45B. Outside surface: blood red, Red Group 45D, dull. Stamens: on the average approximately 140 in number. Anthers: normal, yellow in color at the terminal end. Pistils: on the average approximately 48 in number.

Disease resistance: Good disease resistance.

I claim:

1. A new and distinct variety of Rose plant of the Miniature Class, which is a sport of the Meirov variety, substantially as illustrated and described, characterized by the fact that:

from the physical standpoint the plant has medium green adult wood and a bushy growth habit, and forms double flowers which are blood red in color wherein the petals are yellowish at the base and possess a great degree of substance; and from the biological standpoint the plant has vigorous vegetation, is well adapted to hot culture, is resistant to disease, and has the ability to hold its flowers for a long period of time.

* * * * *